United States Patent
Bräunlich et al.

[11] Patent Number: 5,922,740
[45] Date of Patent: Jul. 13, 1999

[54] HETEROCYCLYLCARBONYL SUBSTITUTED BENZOFURANYL-UREAS

[75] Inventors: Gabriele Bräunlich; Mazen Es-Sayed, both of Wuppertal; Rüdiger Fischer, Köln; Burkhardt Fugmann, Ratingen; Rolf Henning, Wachtberg; Michael Sperzel; Ulrich Nielsch, both of Wuppertal, all of Germany; Graham Sturton, Bray Maidenhead, United Kingdom

[73] Assignee: Bayer Aktiengesellschaft, Leverkusen, Germany

[21] Appl. No.: 08/760,612

[22] Filed: Dec. 4, 1996

[30] Foreign Application Priority Data

Dec. 11, 1995 [GB] United Kingdom .................. 9525262

[51] Int. Cl.$^6$ .......................... C07D 405/06; A61K 31/44
[52] U.S. Cl. .......................... 514/337; 514/365; 514/444; 546/284.1; 544/333; 548/200
[58] Field of Search .................. 546/284.1; 514/337

[56] References Cited

U.S. PATENT DOCUMENTS 4,745,127  5/1988  Atkinson et al. ....................... 514/469

FOREIGN PATENT DOCUMENTS 0 146 243 A1  6/1985  European Pat. Off.
0 731 099 A1  9/1996  European Pat. Off.

OTHER PUBLICATIONS

Biochem.J. 291, 389–395 (1993).

Biochem.Pharmacol. 42, 153–162 (1991).

Eur.J.Pharmacol. 127, 105–115, 1986.

*Primary Examiner*—Jane Fan
*Attorney, Agent, or Firm*—Sprung Kramer Schaefer & Briscoe

[57] ABSTRACT

Heterocyclyclcarbonyl substituted benzofuranyl-ureas are prepared by reacting heterocyclylcarbonyl substituted 3-amino-benzofuranes with appropriate isocyanates or isothiocyanates. The unsubstituted ureas are transferred into substituted ureas by usual methods of substitution. The heterocyclylcarbonyl substituted benzofuranyl-ureas are useful as active ingredients in medicaments particularly for the treatment of acute and chronical inflammatory processes.

6 Claims, No Drawings

HETEROCYCLYLCARBONYL SUBSTITUTED BENZOFURANYL-UREAS

The invention relates to heterocyclylcarbonyl substituted benzofuranyl-ureas, processes for their preparation and their use in medicaments.

It is known that the NADPH oxidase of phagocytes is the physiological source to the superoxide radical anion and reactive oxygen species derived therefrom which are important in the defence against pathogens. Moreover, both inflammatory (e.g. TNFα, IL-1 or IL-6) and anti-inflammatory cytokines (e.g. IL-10) play a pivotal role in host defence mechanisms. Uncontrolled production of inflammatory mediators can lead to acute and chronic inflammation, tissue damage, multi-organ failures and to death. It is additionally known that elevation of phagocyte cyclic AMP leads to inhibition of oxygen radical production and that this cell function is more sensitive than others such as aggregation or enzyme release.

None of the above compounds are taught to possess PDE IV inhibition activity.

Benzofuran- and benzothiophene derivatives having lipoxygenase-inhibiting action are described in the publication EP 146 243.

The invention relates to heterocyclylcarbonyl substituted benzofuranyl-ureas of the general formula (I)

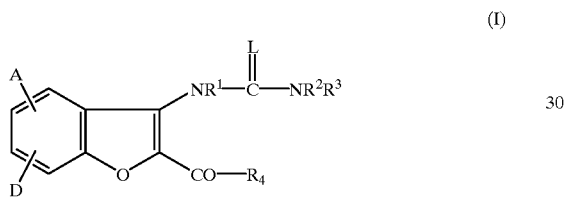

in which

A and D are identical or different and represent hydrogen, straight-chain or branched acyl or alkoxycarbonyl each having up to 6 carbon atoms or straight-chain or branched alkyl having up to 6 carbon atoms, which is optionally substituted by carboxyl or alkoxycarbonyl having up to 6 carbon atoms, phenoxy or benzoyl, or represent halogen, carboxyl, cyano, nitro, trifluoromethyl, trifluoromethoxy or a group of a formula $-OR^5$, $-S(O)_aR^6$, $-(O-CH_2-CO)_b-NR^7R^8$, $-CO-NR^9R^{10}$, $-SO_2-NR^{11}R^{12}$ or $-NH-SO_2R^{13}$, in which $R^6$, $R^8$, $R^{10}$ and $R^{12}$ are identical or different and denote hydrogen, cycloalkyl having 3 to 6 carbon atoms, benzyl or a 5 to 7-membered saturated or unsaturated heterocycle having up to 3 heteroatoms from the series comprising N, S and O and to which a phenyl ring can be fused and which is optionally substituted by identical or different substituents from the series comprising halogen, cyano, nitro or by a straight-chain or branched alkyl having up to 6 carbon atoms or denote straight-chain or branched alkyl, alkenyl or acyl each having up to 8 carbon atoms, or denote phenyl, which is optionally monosubstituted to disubstituted by identical or different substituents from the series comprising nitro, halogen, carboxy or straight-chain or branched alkoxycarbonyl having up to 6 carbon atoms, $R^5$ has the abovementioned meaning of $R^6$, $R^8$, $R^{10}$ or $R^{12}$, or $R^5$ denotes a hydroxyl protecting group or straight-chain or branched alkoxycarbonyl having up to 6 carbon atoms, or denotes straight-chain or branched alkyl having up to 8 carbon atoms, which is substituted by carboxyl, hydroxyl, straight-chain or branched acyl or alkoxycarbonyl each having up to 6 carbon atoms, phenoxy, benzoyl or by a 5- to 7-membered unsaturated heterocycle having up to 3 heteroatoms from the series comprising N, S and/or O, which is optionally substituted by halogen, cyano, nitro, or by straight-chain or branched alkyl having up to 6 carbon atoms, or $R^5$ denotes a group of a formula $-SO_2-R^{13}$ $R^{13}$ denotes aryl having up 6 to 10 carbon atoms, trifluoromethyl or straight-chain or branched alkyl having up to 4 carbon atoms, a denotes a number 0, 1 or 2, b denotes a number 0 or 1, $R^7$, $R^9$ and $R^{11}$ are identical or different and denote hydrogen or a straight-chain or branched alkyl having up to 4 carbon atoms, $R^1$ represents hydrogen, straight-chain or branched alkyl having up to 6 carbon atoms, an aminoprotecting group or a group of the formula $-CO-R^{14}$ in which $R^{14}$ denotes hydroxyl, straight chain or branched alkoxycarbonyl having up to 6 carbon atoms, cycloalkyl having up 3 to 6 carbon atoms, pyridyl, pyrrolidinyl or straight chain or branched alkyl having up to 8 carbon atoms, which is optionally substituted by halogen, carboxyl or straight chain or branched alkoxycarbonyl having up to 6 carbon atoms, or denotes phenyl, which is optionally substituted by hydroxyl, carboxyl or straight chain or branched alkoxy or alkoxycarbonyl each having up to 6 carbon atoms, L represents an oxygen or sulfur atom, $R^2$ and $R^3$ are identical or different and represent hydrogen, cycloalkyl having up to 6 carbon atoms, straight chain or branched alkyl, alkoxycarbonyl or alkenyl each having up to 8 carbon atoms, or represent benzoyl or aryl having 6 to 10 carbon atoms, which are optionally monosubstituted to trisubstituted by identical or different substituents from the series comprising halogen, cyano, nitro, carboxyl, straight-chain or branched alkyl, alkoxy, alkoxycarbonyl or acyl each having up to 6 carbon atoms, or $R^2$ and $R^3$ together with the nitrogen atom form a 5- to 7-membered saturated heterocycle optionally having a further O atom, and $R^4$ represents a 5 to 7 membered, saturated or unsaturated heterocycle, which can contain up to 4 oxygen, sulphur and/or nitrogen atoms as heteroatoms and to which further a benzene ring can be fused and wherein both rings are optionally monosubstituted to trisubstituted by identical or different substituents from the series comprising hydroxyl, halogen, nitro, 1H-tetrazolyl, pyridyl, trifluoromethyl, trifluoromethoxy, difluoromethyl, difluoromethoxy, cyano, carboxy, straight-chain or branched alkoxy, alkoxycarbonyl or acyl each having up to 8 carbon atoms or by straight-chain or branched alkyl having up to 6 carbon atoms, which is optionally substituted by carboxyl or straight-chain or branched alkoxycarbonyl having up to 5 carbon atoms or by a group of formula —NR$^{15}$R$^{16}$, —SR$^{17}$, SO$_2$R$^{18}$ or —O—SO$_2$R$^{19}$, in which R$^{15}$ and R$^{16}$ have the meaning shown above for R$^7$ and R$^8$ and are identical or different from the latter, or R$^{15}$ denotes hydrogen and R$^{16}$ denotes straight-chain or branched acyl having up to 6 carbon atoms R$^{17}$ denotes straight-chain or branched alkyl having up to 6 carbon atoms, R$^{18}$ and R$^{19}$ are identical or different and represent straight-chain or branched alkyl having up to 6 carbon atoms, benzyl or phenyl, which are optionally substituted by trifluoromethyl, halogen or straight-chain or branched alkyl having up to 6 carbon atoms, and salts thereof.

The heterocyclylcarbonyl substituted benzofuranyl-ureas according to the invention can also be present in the form of their salts and pyridinium salts. In general, salts with organic or inorganic bases or acids may be mentioned here.

Physiologically acceptable salts are preferred in the context of the present invention. Physiologically acceptable salts of the heterocyclylcarbonyl substituted benzofuranyl-ureas can be metal or ammonium salts of the substances according to the invention, which contain a free carboxylic group. Those which are particularly preferred are, for example, sodium, potassium, magnesium or calcium salts, and also ammonium salts which are derived from ammonia, or organic amines, such as, for example, ethylamine, di- or triethylamine, di- or triethanolamine, dicyclohexylamine, dimethylaminoethanol, arginine, lysine or ethylenediamine.

Physiologically acceptable salts can also be salts of the compounds according to the invention with inorganic or organic acids. Preferred salts here are those with inorganic acids such as, for example, hydrochloric acid, hydrobromic acid, phosphoric acid or sulphuric acid, or salts with organic carboxylic or sulphonic acids such as, for example, acetic acid, maleic acid, fumaric acid, malic acid, citric acid, tartaric acid, ethanesulphonic acid, benzenesulphonic acid, toluenesulphonic acid or naphthalenedisulphonic acid. Also preferred pyridinium salts are salts in combination with halogen.

The compounds according to the invention can exist in stereoisomeric forms which either behave as image and mirror image (enantiomers), or which do not behave as image and mirror image (diastereomers). The invention relates both to the antipodes and to the racemate forms, as well as the diastereomer mixtures. The racemate forms, like the diastereomers, can be separated into the stereoisomerically uniform constituents in a known manner.

Heterocycle in general represents a 5- to 7-membered saturated or unsaturated, preferably 5- to 6-membered, saturated or unsaturated ring which can contain up to 3 oxygen, sulphur and/or nitrogen atoms as heteroatoms and to which further aromatic ring can be fused.

The following are mentioned as preferred: thienyl, furyl, pyrrolyl, pyridyl, pyrimidyl, pyrazinyl, pyridazinyl, quinolyl, isoquinolyl, quinazolyl, quinoxazolyl, cinnolyl, thiazolyl, dihydrothiazolyl, benzothiaazolyl, isothiazolyl, benzisothiazolyl, oxazolyl, benzoxazolyl, isoxazolyl, imidazolyl, benzimidazolyl, indolyl, morpholinyl, pyrrolidinyl, piperidyl, piperazinyl, oxazolyl, oxazolinyl or triazolyl.

Amino protective group in the context of the above mentioned definition in general represents a protective group from the series comprising:

benzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 4-nitrobenzyloxycarbonyl, 2-nitrobenzyloxycarbonyl, 2-nitro-4,5-dimethoxybenzyloxycarbonyl, methoxycarbonyl, ethoxycarbonyl, propoxycarbonyl, isopropoxycarbonyl, butoxycarbonyl, isobutoxycarbonyl, tert.butoxycarbonyl, allyloxycarbonyl, vinyloxycarbonyl, 2-nitrobenzyloxycarbonyl, 3,4,5-trimethoxybenzyloxycarbonyl, cyclohexoxycarbonyl, 1,1-dimethylethoxycarbonyl, adamantylcarbonyl, phthaloyl, 2,2,2-trichlorethoxycarbonyl, 2,2,2-trichlor-tertbutoxycarbonyl, menthyloxycarbonyl, phenoxycarbonyl, 4-nitrophenoxycarbonyl, fluorenyl-9-methoxycarbonyl, formyl, acetyl, propionyl, pivaloyl, 2-chloracetyl, 2-bromacetyl, 2,2,2-trifluoracetyl, 2,2,2-trichloracetyl, benzoyl, 4-chlorbenzoyl, 4-brombenzoyl, 4-nitrobenzoyl, phthalirnido, isovaleroyl oder benzyloxymethylen, 4-nitrobenzyl, 2,4-dinitrobenzyl or 4-nitrophenyl.

Preferred compounds of the general formula (I) are those in which

A and D are identical or different and represent hydrogen, straight-chain or branched acyl or alkoxycarbonyl each having up to 6 carbon atoms, or straight-chain or branched alkyl having up to 4 carbon atoms, which is optionally substituted by carboxyl or alkoxycarbonyl having up to 5 carbon atoms, phenoxy or benzoyl, or represent fluorine, chlorine, bromine, nitro, trifluoromethyl or a group of a formula —OR$^5$, —S(O)$_a$R$^6$, (O—CH$_2$—CO)$_b$—NR$^7$R$^8$, —CO—NR$^9$R$^{10}$, —SO$_2$—NR$^{11}$R$^{12}$ or —NH—SO$_2$R$^{13}$, in which R$^6$, R$^8$, R$^{10}$ and R$^{12}$ are identical or different and denote hydrogen, cyclopropyl, cyclopentyl, cyclohexyl, chinolyl, pyridyl, imidazolyl, 1,3-thiazolyl or thienyl, which are optionally substituted by identical or different substituents from the series comprising fluorine, chlorine, bromine, iodine, cyano, nitro or by a straight-chain or branched alkyl having up to 5 carbon atoms, denote straight-chain or branched alkyl, alkenyl or acyl each having up to 6 carbon atoms, or denote phenyl, which is optionally monosubstituted to disubstituted by identical or different substituents from the series comprising nitro, fluorine, chlorine, bromine, iodine, carboxyl or straight-chain or branched alkoxycarbonyl having up to 5 carbon atoms, R$^5$ has the abovementioned meaning of R$^6$, R$^8$, R$^{10}$ or R$^{12}$, or R$^5$ denotes benzyl, acetyl or tetrahydropyranyl or straight chain or branched alkoxycarbonyl having up to 4 carbon atoms, denotes straight-chain or branched alkyl having up to 6 carbon atoms, which is optionally substituted by carboxyl, hydroxyl, straight-chain or branched acyl or alkoxycarbonyl each having up to 4 carbon atoms, phenoxy, benzoyl or by pyridyl, imidazolyl, thenyl or furyl, which are optionally substituted by fluorine, chlorine, bromine, cyano, nitro or by straight-chain or branched alkyl having up to 4 carbon atoms, or R$^5$ denotes a group of a formula —SO$_2$R$^{13}$, R$^{13}$ denotes phenyl, trifluormethyl or straight-chain or branched alkyl having up to 3 carbon atoms, a denotes a number 0, 1 or 2, b denotes a number 0 or 1, $R^7$, $R^9$ and $R^{11}$ are identical or different and denote hydrogen or a straight-chain or branched alkyl having up to 3 carbon atoms, $R^1$ represents hydrogen, straight-chain or branched alkyl having up to 4 carbon atoms, tertbutoxycarbonyl or a group of the formula —CO—$R^{14}$ in which $R^{14}$ denotes hydroxyl, straight chain or branched alkoxycarbonyl having up to 4 carbon atoms, cyclopentyl, cyclohexyl, pyridyl, pyrrolidinyl or straight chain or branched alkyl having up to 5 carbon atoms, which is optionally substituted by fluorine, chlorine, bromine, carboxyl or straight chain or branched alkoxycarbonyl having up to 4 carbon atoms, or denotes phenyl, which is optionally substituted by hydroxyl, carboxyl or straight chain or branched alkoxy or alkoxycarbonyl each having up to 4 carbon atoms, L represents an oxygen or sulfur atom, $R^2$ and $R^3$ are identical or different and represent hydrogen, cyclobutyl, cyclopentyl, cyclohexyl or straight-chain or branched alkyl, alkoxycarbonyl or alkenyl each having up to 6 carbon atoms, or represent benzoyl or phenyl, which are optionally monosubstituted to trisubstituted by identical or different substituents from the series comprising fluorine, chlorine, bromine, iodine, carboxyl, cyano, nitro or by a straight-chain or branched alkyl, alkoxy or alkoxycarbonyl each having up to 5 carbon atoms, or $R^2$ and $R^3$ together with the nitrogen atom form a pyrrolidinyl, piperidinyl or morpholinyl ring, and $R^4$ represents pyridyl, pyrimidyl, pyrryl, imidazolyl, pyrazolyl, thienyl, isothiazolyl, pyrazinyl, thiazolyl or benzo[b]thiophenyl, wherein both rings are optionally monosubstituted to trisubstituted by identical or different substituents from the series comprising hydroxyl, fluorine, chlorine, bromine, nitro, tetrazolyl, pyridyl, trifluoromethyl, trifluoromethoxy, difluoromethyl, difluoromethoxy, cyano, carboxy, straight-chain or branched alkoxy, alkoxycarbonyl or acyl each having up to 6 carbon atoms, or by straight-chain or branched alkyl having up to 4 carbon atoms, which is optionally substituted by carboxyl or straight-chain or branched alkoxycarbonyl having up to 4 carbon atoms and salts thereof.

Particularly preferred compounds of the general formula (I) are those in which

A and D are identical or different and represent hydrogen, straight-chain or branched alkoxycarbonyl having up to 4 carbon atoms, straight-chain or branched alkyl having up to 3 carbon atoms, which is optionally substituted by carboxyl or alkoxycarbonyl each having up to 4 carbon atoms, phenoxy or benzoyl, or represent fluorine, chlorine, bromine, carboxyl, cyano, nitro, trifluoromethyl, trifluoromethoxy or a group of a formula —$OR^5$, in which $R^5$ denotes hydrogen or straight-chain or branched alkyl or alkenyl each having up to 6 carbon atoms, $R^1$ represents hydrogen or straight-chain or branched alkyl having up to 3 carbon atoms or a group of the formula —CO—$R^{14}$, in which $R^{14}$ denotes hydroxyl or straight chain or branched alkoxycarbonyl having up to 3 carbon atoms, L represents an oxygen or sulfur atom, $R^2$ and $R^3$ are identical or different and represent hydrogen, straight-chain or branched alkyl, alkoxycarbonyl or alkenyl each having up to 5 carbon atoms, or represent benzoyl or phenyl, which are optionally substituted by identical or different substituents from the series comprising fluorine, chlorine, bromine, carboxy, cyano, nitro or by a straight-chain or branched alkyl, alkoxy or alkoxycarbonyl each having up to 3 carbon atoms, and $R^4$ represents pyridyl, pyrimidyl, furyl, thienyl, imidazolyl, pyrrolyl, thiazolyl or pyrazinyl which are optionally up to trifold substituted by identical or different, substituents from the series comprising pyridyl, fluorine, chlorine, bromine, methoxy, nitro, trifluoromethyl, cyano, or by straight-chain or branched alkyl having up to 3 carbon atoms, which is optionally substituted by carboxyl or straight-chain or branched alkoxycarbonyl having up to 3 carbon atoms, and salts thereof.

Very particularly preferred compounds of the general formula (I) are those in which A and D are identical or different and represent hydrogen, straight-chain or branched alkyl or alkenyl each having up to 3 carbon atoms, or represent fluorine, chlorine, bromine, carboxyl, cyano, nitro, trifluoromethyl, trifluoromethoxy or methoxy $R^1$ represents hydrogen or, in which L represents an oxygen or sulfur atom, $R^2$ and $R^3$ are identical or different and represent hydrogen alkoxycarbonyl having up to 4 carbon atoms, and $R^4$ represents pyridyl, furyl, thienyl or thiazolyl which are optionally up to twofold substituted by identical or different, substituents from the series comprising fluorine, chlorine, bromine, iodine, nitro, methoxy, trifluoromethyl, cyano, or by straight-chain or branched alkyl having up to 3 carbon atoms, and salts thereof A process for the preparation of the compounds of the general formula (I) has additionally been found, characterized in that compounds of the general formula (II)

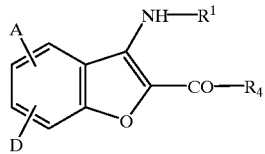

(II)

in which

A, D, $R^1$ and $R^4$ have the abovementioned meaning are reacted with compounds of the general formula (III)

$R^2$—N=C=L (III)

in which

L and $R^2$ have the abovementioned meaning in inert solvents, if appropriate in the presence of a base and/or in the presence of an auxiliary, and in the case of $R^2/R^3$=H and L=O,
compounds of the general formula (II) are reacted with compounds of the general formula (IIIa)

$$E-SO_2-N=C=O \quad \text{(IIIa)}$$

in which
E denotes halogen, preferably chlorine,
and in the case of $R^2/R^3$=H and L=S,
compounds of the general formula (II) are reacted with $NH_4SCN$,
and in case of $R^1$, $R^2$ and/or $R^3 \neq H$ the amino groups are derivated optionally by customary methods.

The process according to the invention can be illustrated by way of example by the following equations:

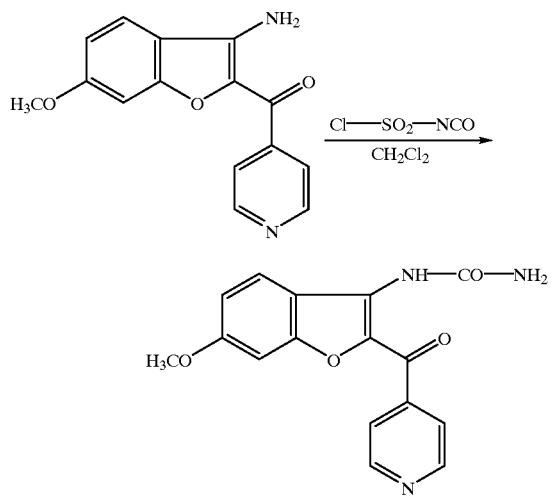

Suitable solvents are generally customary organic solvents which do not change under the reaction conditions. These include ethers such as diethyl ether, dioxane or tetrahydrofurane, ethylacetate, acetone, dimethylsulfoxide, dimethylformamide or alcohols such as methanol, ethanol, propanol or halogenohydrocarbons such as dichloromethane, dichloroethane, trichloromethane or tetrachloromethane. Dichloromethane is preferred.

Suitable bases are generally inorganic or organic bases. These preferably include alkali metal hydroxides such as, for example, sodium hydroxide, sodium hydrogen-carbonate or potassium hydroxide, alkaline earth metal hydroxides such as, for example, barium hydroxide, alkali metal carbonates such as sodium carbonate, potassium carbonate, alkaline earth metal carbonates such as calcium carbonate, or alkaline metal or organic amines (trialkyl($C_1$–$C_6$)amines) such as triethylamine, or heterocycles such as 1,4-diazabicyclo[2.2.2]octane (DABCO), 1,8-diazabicyclo[5.4.0]undec-7-ene (DBU), or amides such as sodium amides, lithium butyl amide or butyllithium, pyridine or methylpiperidine. It is also possible to employ alkali metals, such as sodium or its hydrides such as sodium hydride, as bases. Potassium carbonate, triethylamine, sodium hydrogencarbonate and sodium-hydroxide are preferred.

The process is in general carried out in a temperature range from –30° C. to +100° C., preferably from –10° C. to +50° C.

The process is generally carried out at normal pressure. However, it is also possible to carry out it at elevated pressure or at reduced pressure (for example in a range from 0.5 to 5 bar).

The base is employed in an amount from 1 mol to 10 mol, preferably from 1.0 mol to 4 mol, relative to 1 mol of the compounds of the general formulae (III) or (IIIa).

The compounds of the general formula (II) are new or are prepared by at first reacting compounds of the general formula (IV)

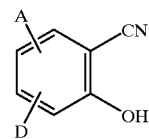

in which
A and D have the abovementioned meaning
with compounds of the general formula (V)

$$R^4-CO-CH_2-T \quad \text{(V)}$$

in which
$R^4$ has the abovementioned meaning and
T represents a typical leaving group such as, for example, chlorine, bromine, iodine, tosylate or mesylate, preferably bromine,
to prepare compounds of the general formula (VI)

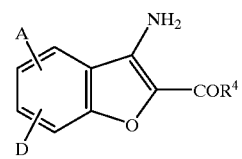

in which
A, D and $R^4$ have the abovementioned meaning,
in one of the abovementioned solvents and bases, preferably potassium carbonate and dimethylformamide or acetone, and in the case of $R^1 \neq H$ the abovementioned substitutents are introduced by customary methods.

The process is in general carried out in a temperature range from +10° C. to +150° C., preferably from +50° C. to +100° C.

The process is generally carried out at normal pressure. However, it is also possible to carry out it at elevated pressure or at reduced pressure (for example in a range from 0.5 to 5 bar).

The compounds of the general formulae (III), (IIIa), (IV), (V) and (VI) are known or can be prepared by customary methods.

Surprisingly it was found that compounds of the general formula (I) inhibited oxygen radical formation as well as TNFα (tumor necrosis factor) production. These compounds elevated cellular cyclic AMP probably by inhibition of phagocyte phosphodiesterase activity.

The compounds according to the invention specifically inhibit the production of superoxide by polymorphonuclear leukocytes (PMNL). Futhermore, these compounds inhibit TNFα release in human monocytes in response to a variety of stimuli including bacterial lipopolysaccharide (LPS), complement-opsonized zymosan (ZymC3b) and IL-1β. The described effects are probably mediated by the elevation of cellular cAMP due to inhibition of the type IV phosphodiesterase responsible for its degradation.

They can therefore be employed in medicaments for the treatment of acute and chronic inflammatory processes.

The compounds according to the invention are preferably suitable for the treatment and prevention of acute and chronic inflammation and auto immune diseases, such as emphysema, alveolitis, shock lung, all kind of COPD, ARDS, asthma and bronchitis, cystic fibrosis, eosinophilic granuloma, arteriosclerosis, arthrosis, inflammations of the gastrointestinal tract, myocarditis, bone resorption diseases, reperfusion injury, Crohn's disease, ulcerative colitis, system lupus erythematosus, type I diabetes mellitus, psoriasis, anaphylactoid purpura nephritis, chronic glomerulonephtritis, inflammatory bowel disease, other benign and malignant proliferative skin diseases, atopic dermatitis, allergic rhinitis, allergic conjunctivitis, vernal conjuctivitis, arterial restenosis, sepsis and septic shock, toxic shock syndrome, grafts vs host reaction, allograft rejection, treatment of cytokine mediated chronic tissue degeneration, rheumatoid arthritis, arthritis, rheumatoid spondylitis and osteoarthritis and coronary insufficiency, myalgias, multiple schlerosis, malaria, AIDS, cachexia, prevention of tumor growth and invasion of tissue, leukemia, depression, memory impairment and acute stroke. The compounds according to the invention are additionally suitable for reducing the damage to infarct tissue after reoxygenation. In this case the simultaneous administration of allopurinol to inhibit xanthine oxidase is of advantage. Combination therapy with superoxide dismutase is also of use.

Test Description

1. Preparation of Human PMNL

Blood was taken from healthy subjects by venous puncture and neutrophils were purified by dextran sedimentation and resuspended in the buffered medium.

2. Inhibition of FMLP-stimulated Production of Superoxide Racidal Anions.

Neutrophils ($2.5 \times 10^5$ ml$^{-1}$) were mixed with cytochrome C (1.2 mg/ml) in the wells of a microtitre plate. Compounds according to the invention were added in dimethyl sulphoxide (DMSO). Compound concentration ranged from 2.5 nM to 10 µM, the DMSO concentration was 0.1% v/v in all wells. After addition of cytochalasin b (5 µgxml$^{-1}$) the plate was incubated for 5 min at 37° C. Neutrophils were then stimulated by addition of $4 \times 10^{-8}$M FMLP and superoxide generation measured as superoxide dismutase inhibitable reduction of cytochrome C by monitoring the OD$_{550}$ in a Thermomax microtitre plate spectrophotometer. Initial rates were calculated using a Softmax kinetic calculation programme. Blank wells contained 200 units of superoxide dismutase.

The inhibition of superoxide production was calculated as follows:

$$\frac{[1 - ((Rx - Rb))]}{((Ro - Rb))} \cdot 100$$

Rx=Rate of the well containing the compound according to the invention.
Ro=Rate in the control well.
Rb=Rate in the superoxide dismutase containing blank well.

Compounds according to the invention have IC$_{50}$ values in the range 0.07 µM–10 µM.

3. Measurement of PMNL Cyclic AMP Concentration

The compounds according to the invention were incubated with $3.7 \times 10^6$ PMNL for 5 min at 37° C. before addition of $4 \times 10^{-8}$M FMLP. After 6 min protein was precipitated by the addition of 1% v/v conc. HCl in 96% v/v ethanol containing 0.1 mM EDTA. After centrifugation the ethanolic extracts were evaporated to dryness under N$_2$ and resuspended in 50 mM Tris/HCl pH 7.4 containing 4 mM EDTA. The cyclic AMP concentration in the extracts was determined using a cyclic AMP binding protein assay supplied by Amersham International plc. Cyclic AMP concentrations were expressed as percentage of vehicle containing control incubations.

Compounds elavate the cAMP-level at 1 µM compound 0–400% of control values.

4. Assay of PMNL Phosphodiesterase

This was performed as a particulate fraction from human PMN essentially as described by Souness and Scott (Biochem. J. 291, 389–395, 1993). Particulate fractions were treated with sodium vanadate/glutathione as described by the authors to express the descrete stereospecific site on the phosphodiesterase enzyme. Compounds according to the invention had IC$_{50}$ values ranging from 0.001 µM to 10 µM.

5. Assay of Human Platelet Phosphodiesterase

This was performed essentially as described by Schmidt et al (Biochem. Pharmacol. 42, 153–162, 1991) except that the homogenate was treated with vanadate glutathione as above. Compounds according to the invention had IC$_{50}$ values greater than 100 µM.

6. Assay of Binding to the Rolipram Binding Site in Rat Brain Membranes

This was performed essentially as described by Schneider et al. (Eur. J. Pharmacol. 127, 105–115, 1986). Compounds according to the invention had IC$_{50}$ values in the range 0.01 to 10 µM.

7. Preparation of Human Monocytes

Blood was taken from normal donors. Monocytes were isolated from peripheral blood by density centrifugation, followed by centrifugal elutriation.

8. Endotoxin Induced TNF Release

Monocytes ($1 \times 10^6$ ml$^{-1}$) were stimulated with LPS (2 µg ml$^{-1}$) and coincubated with the compounds at different concentrations ($10^{-4}$ to 10 µg ml$^{-1}$) Compounds were dissolved in DMSO/medium (2% v/v). The cells were incubated in RPMI-1640 medium glutamine/FCS supplemented and at 37° C. in a humidified atmosphere with 5% CO$_2$. After 18 to 24 hours TNF was determined in the supernatants by an human TNF specific ELISA (medgenix). Controls were nonstimulated and LPS stimulated monocytes without compounds. Example 2, 13 and 16 induce inhibition of LPS driven TNF activity in human monocytes (IC$_{50}$: $10^{-3}$ to 1 µg ml$^{-1}$).

9. Endotoxin Induced Shock Lethality in Mice

B6D2F1 mice (n=10) were sensitized with galactosamine (600 mg/kg), and shock and lethality were triggered by LPS (0.01 µg/mouse). The compounds were administered intravenously 1 hour prior LPS. Controls were LPS challenged mice without compound. Mice were dying 8 to 24 hours post LPS challenge. Example 2, 13 and 16 reduced the endotoxin medicated mortality about 70% to 100% at doses of 3 to 30 mg/kg.

The galactosamine/LPS mediated mortality was reduced.

The new active compounds can be converted into a known manner into the customary formulations, such as tablets, coated tablets, pills, granules, aerosols, syrups, emulsions, suspensions and solutions, using inert, nontoxic, pharmaceutically suitable excipients or solvents. In this connection, the therapeutically active compound should in each case be present in a concentration of about 0.5 to 90% by weight of the total mixture, i.e. in amounts which are sufficient in order to achieve the dosage range indicated.

The formulations are prepared, for example, by extending the active compounds with solvents and/or excipients, if appropriate using emulsifiers and/or dispersants, where, for example, in the case of the use of water as a diluent, organic solvents can be used as auxiliary solvents if appropriate.

Administration is carried out in a customary manner, preferably orally or parenterally, in particular perlingually or intravenously.

In the case of parenteral administration, solutions of the active compound can be employed using suitable liquid vehicles.

In general, it has proved advantageous on intravenous administration to administer amounts from about 0.001 to 10 mg/kg, preferably about 0.01 to 5 mg/kg of body weight to achieve effective results, and on oral administration the dosage is about 0.01 to 25 mg/kg, preferably 0.1 to 10 mg/kg of body weight.

In spite of this, it may be necessary to depart from the amounts mentioned, in particular depending on the body weight or the type of application route, on individual behaviour towards the medicament, the manner of its formulation and the time or interval at which administration takes place. Thus, in some cases it may be sufficient to manage with less than the abovementioned minimum amount, while in other cases the upper limit mentioned must be exceeded. In the case of administration of relatively large amounts, it is advisable to divide these into several individual doses over the course of the day.

| | Solvents | |
|---|---|---|
| I | petrolether:ethylacetate | 1:1 |
| II | petrolether:ethylacetate | 5:1 |
| III | petrolether:ethylacetate | 5:2 |
| IV | ethylacetate | |
| V | dichlormethane:methanol | 5:1 |
| VI | dichlormethane | |

| | Solvents | |
|---|---|---|
| VII | cyclohexane:ethylacetate | 3:1 |
| VIII | dichlormethane:methanol | 50:1 |
| IX | dichlormethane:methanol | 20:1 |
| X | dichloromethane:methanol:17% NH$_3$(aq.) | 15:4:0.5 |
| XI | dichlormethane:methanol:NH$_3$ | 75:20:2.5 |
| XII | cyclohexane:tetrahydrofurane | 3:7 |
| XIII | dichlormethane:methanol | 9:1 |

Starting Compounds

EXAMPLE I (3-Amino-5-methoxy-benzofuran-2-yl)-pyridin-3-yl-methadone

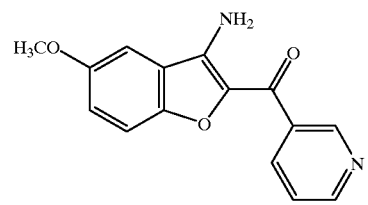

4 g (0.27 mmol) of 2-Hydroxy-5-methoxy-benzonitrile and 10.6 g (0.77 mmol) potassium carbonate were suspended in 70 ml acetone and 8.7 ml (0.31 mmol) 4-Bromo-3-acetylpyridine were added in 3 portions during 1 hour. The mixture was heated to reflux for 12 hours. The mixture was filtered hot. The solvens was destined of in vacuo and the residue recrystallized in methanol.

Yield: 3.16 g (44%); Mp.: 168° C.

The compounds shown in table I are prepared in analogy to example I.

TABLE I

| Ex.-No. | X | Y | Z | R$^4$ | Mp. (° C.) | Yield (% of theory) | R$_f$ |
|---|---|---|---|---|---|---|---|
| II | H | OCH$_3$ | H | (4-pyridyl) | 241 | 23 | 0.07 (III) |
| III | H | OCH$_3$ | H | (3-pyridyl) | 198 | 30 | 0.08 (III) |
| IV | H | OCH$_3$ | H | (pyrazinyl) | 193 | 48 | 0.17 (III) |

TABLE I-continued

| Ex.-No. | X | Y | Z | R4 | Mp. (° C.) | Yield (% of theory) | $R_f$ |
|---|---|---|---|---|---|---|---|
| V | H | OCH₃ | H | 2-pyridyl | 142 | 15 | 0.66 (II) |
| VI | Cl | OCH₃ | H | 3-pyridyl | 268 | 88 | 0.38 (V) |
| VII | Cl | OCH₃ | H | 4-pyridyl | 248 | 72 | 0.26 (V) |
| VIII | OCH₃ | H | H | 4-pyridyl | 158 | 13 | 0.48 (V) |
| IX | H | OCH₃ | H | 2-thienyl | 125 | 77 | 0.28 (V) |
| X | OCH₃ | H | H | 2-pyridyl | — | 18 | 0.33 (IX) |
| XI | H | CH₃ | H | 3-pyridyl | 155 | 59 | |
| XII | H | CH₃ | H | 4-pyridyl | 224 | 60 | |
| XIII | H | OCH₃ | H | 2-thiazolyl | 216 | 30 | 0.07 (III) |
| XIV | OCH₃ | H | H | 3-thienyl | 202 | 37 | 0.23 (IIII) |

TABLE I-continued

| Ex.-No. | X | Y | Z | R4 | Mp. (° C.) | Yield (% of theory) | $R_f$ |
|---|---|---|---|---|---|---|---|
| XV | H | OCH₃ | H | 5-bromo-3-methylpyridin-3-yl | 225 | 42 | 0.58 (I) |
| XVI | H | OCH₃ | H | 2,5-dimethylfuran-3-yl | 135 | 60 | 0.60 (I) |
| XVII | H | CF3 | H | pyridin-3-yl | 163 | 67 | 0.41 (I) |
| XVIII | F | NO₂ | H | pyridin-3-yl | 222 | 28 | 0.28 (I) |
| XIX | H | OCH₃ | H | 5-chloro-2-methylthiophen-3-yl | 192 | 55 | 0.78 (I) |
| XX | H | OCH₃ | H | 2,4,6-trimethylpyridin-3-yl | 166 | 65 | 0.17 (IX) |
| XXI | H | OCH₃ | H | 2,5-dichloro-4-methylthiophen-3-yl | Z. 143 | 53 | 0.74 (I) |
| XXII | H | OCH₃ | H | 3,4-dibromo-5-methylthiophen-2-yl | 196 | 36 | 0.67 (I) |
| XXIII | H | OCH₃ | H | 3-bromo-5-methylthiophen-2-yl | 146 | 50 | 0.67 (I) |

TABLE I-continued
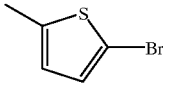
| Ex.-No. | X | Y | Z | R4 | Mp. (°C.) | Yield (% of theory) | $R_f$ |
|---|---|---|---|---|---|---|---|
| XXIV | H | OCH₃ | H | 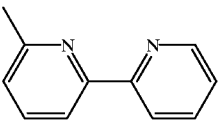 | 180 | 27 | 0.67 (I) |
| XXV | H | OCH₃ | H | 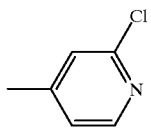 | Z. 156 | 8 | 0.04 (cyclohexan/acetone 1:1) |
| XXVI | H | OCH₃ | H | 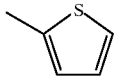 | 153 | 27 | 0.45 (I) |
| XXVII | H | CN | H | 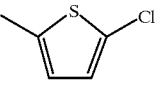 | 228 | 42 | 0.65 (I) |
| XXVIII | H | NO₂ | H | 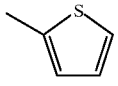 | 273 | 63 | 0.75 (I) |
| XXIX | H | NO₂ | H | 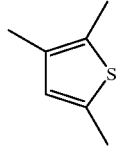 | 265 | 58 | 0.7 (I) |
| XXX | H | OCH₃ | H | 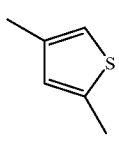 | 159 | 68 | 0.67 (I) |
| XXXI | H | OCH₃ | H | 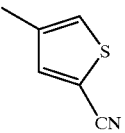 | 112 | 41 | 0.65 (I) |
| XXXII | H | OCH₃ | H |  | 217–220 | 48 | 0.57 (I) |

TABLE I-continued

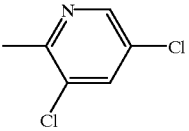

| Ex.-No. | X | Y | Z | R4 | Mp. (° C.) | Yield (% of theory) | $R_f$ |
|---|---|---|---|---|---|---|---|
| XXXIII | H | OCH₃ | H | 2-methyl-3,5-dichloropyridinyl | 76–78 | 88 | 0.54 (IX) |

Preparation Examples

Example 1

[5-Methoxy-2-(pyridine-3-carbonyl)-benzofuran-3-yl]-urea

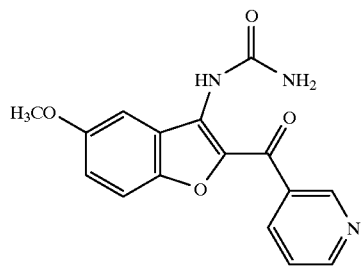

1 g (3.7 mmol) compound of example II was dissolved in dichloromethane (20 ml), cooled to 0° C. and chlorosulphonylisocyanate (0.53 g, 3.7 mmol) in dichloromethane (10 ml) was added dropwise over 30 min., after which the reaction was brought to room temperature and stirred for an additional 4 h. Water (20 ml) was added and the reaction stirred overnight. The precipitate was filtered off, washed with water and dried. Recrystallisation with methylene chloride afford 0.26 g (17%) of the urea.

$R_f$=0.08 (III); Mp.=168° C.

The compounds shown in table 1 are prepared in analogy to example 1.

TABLE 1

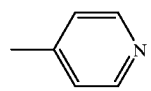

| Ex.-No. | X | Y | Z | R4 | Mp. (° C.) | Yield (% of theory) | $R_f$ |
|---|---|---|---|---|---|---|---|
| 2 | H | OCH₃ | H | 4-pyridinyl | 221 | 69 | 0.2 (V) |
| 3 | H | OCH₃ | H | 3-pyridinyl | 218 | 68 | 0.05 (III) |

TABLE 1-continued
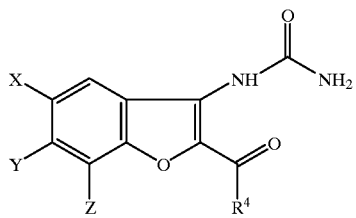
| Ex.-No. | X | Y | Z | R4 | Mp. (° C.) | Yield (% of theory) | $R_f$ |
|---|---|---|---|---|---|---|---|
| 4 | H | OCH₃ | H | 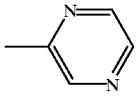 | 250 (Z) | 33 | 0.5 (V) |
| 5 | H | OCH₃ | H | 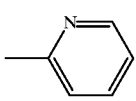 | 180 | 91 | 0.1 (III) |
| 6 | OCH₃ | H | H | 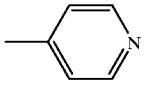 | 178 | 47 | 0.5 (V) |
| 7 | H | OCH₃ | H | 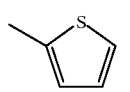 | 232 | 64 | 0.08 (III) |
| 8 | OCH₃ | H | H | 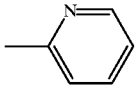 | | | |
| 9 | OCH₃ | H | H | 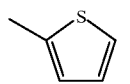 | 232 | 95 | 0.12 (III) |
| 10 | Cl | OCH₃ | H | 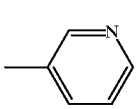 | 222 | 87 | — |
| 11 | Cl | OCH₃ | H | 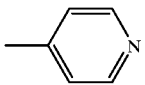 | | | |
| 12* | H | OCH₃ | H | 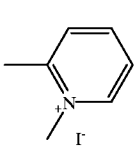 | 199 | 70 | 0.50 (X) |

TABLE 1-continued

[Structure: benzofuran with X, Y, Z substituents on benzene ring; 3-position has NH-C(=O)-NH₂ (urea); 2-position has C(=O)-R⁴; O in furan ring]

| Ex.-No. | X | Y | Z | R⁴ | Mp. (°C.) | Yield (% of theory) | R_f |
|---|---|---|---|---|---|---|---|
| 13* | H | OCH₃ | H | 1-ethyl-4-methylpyridinium Br⁻ | 192 | 42 | 0.11 (X) |
| 14* | H | OCH₃ | H | 1,4-dimethylpyridinium I⁻ | 218 | 88 | 0.30 (X) |
| 15* | H | OCH₃ | H | 1,3-dimethylpyridinium I⁻ | 210 | 79 | 0.30 (X) |
| 16 | H | CH₃ | H | 3-methylpyridine | 258 | 15 | |
| 17 | H | CH₃ | H | 4-methylpyridine | 177 | 10 | |
| 18* | H | OCH₃ | H | 4-methyl-1-(CH₂CO₂CH₃)pyridinium Br⁻ | 169 | 86 | 0.28 (X) |
| 19* | H | OCH₃ | H | 1-ethyl-3-methylpyridinium I⁻ | 177 | 94 | 0.04 (X) |
| 20 | H | OCH₃ | H | 2-methylthiazole | 310 (Z) | 44 | 0.80 (X) |
| 21 | OCH₃ | H | H | 3-methylthiophene | 232 | 95 | 0.11 (III) |

TABLE 1-continued

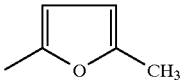

| Ex.-No. | X | Y | Z | R⁴ | Mp. (° C.) | Yield (% of theory) | $R_f$ |
|---|---|---|---|---|---|---|---|
| 22 | H | OCH₃ | H | 5-methyl-furan-2-yl | 232 | 12 | 0.60 (I) |
| 23 | H | CF₃ | H | pyridin-3-yl | 183 | 67 | 0.57 (X) |
| 24 | H | OCH₃ | H | 5-bromo-pyridin-3-yl | 158 (Z) | 48 | 0.15 (X) |
| 25 | F | NO₂ | H | pyridin-3-yl | 246 | 30 | 0.25 (I) |

*0.5 Mmol of pyridine (2-, 3,- or 4-substituted with benzofuranylcarbonyl) are dissolved in 20–100 ml of dry DMF and stirred at room temp. for 1–3 h with 1 mmol of alkyl halide. In the case of slowly reacting compounds (TLC-control), the reaction times are prolonged to 24–48 h at rt or alternatively, the reaction mixtures are heated to 70° C. for 2–6 h. The solutions are concentrated i.vac., the residues triturated with acetone or isopropanol, filtered and dried i.vac.

Example 26

{[5-Methoxy-2-(pyridine-2-carbonyl)-benzofuran-3-yl]-aminothioxomethyl}-carbamic acid ethylester

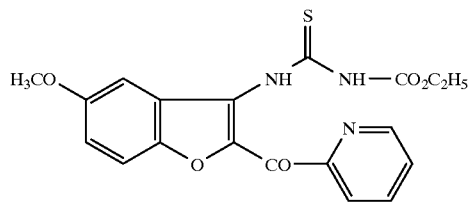

0.4 g (1.49 mmol) of Example X was suspended in 5 ml methylene chloride. After adding of 0.18 ml (1.99 mmol) ethoxycarbonylisothiocyanat the mixture was stirred for one hour at room temperature. The precipitate was filtered off and dried.

Yield=0.335 g (56.3%); $R_f$=0.56 (VIII)

The compounds shown in table 2 are prepared in analogy to example 26.

TABLE 2
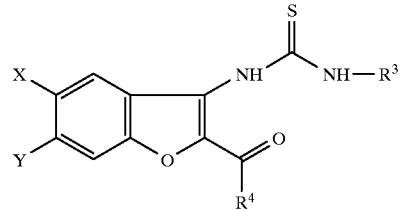
| Ex.-No. | R³ | R⁴ | X | Y | Yield (% of theory) | $R_f$ |
|---|---|---|---|---|---|---|
| 27 | COOC$_2$H$_5$ | 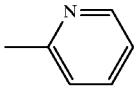 | H | OCH$_3$ | 87 | 0.52 (VIII) |
The compounds shown in table 3 are prepared in analogy to example 1.
TABLE 3
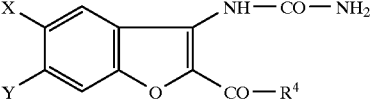
| Ex.-No. | Y | X | R⁴ | $R_f$ | Mp ° C. | Yield (% of theory) |
|---|---|---|---|---|---|---|
| 28 | OCH$_3$ | H | 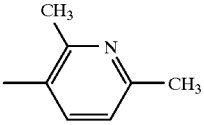 | 0.47 (IX) | 203 (Z) | 27 |
| 29 | NO$_2$ | F | 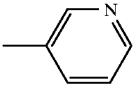 | | | |
| 30 | OCH$_3$ | H | 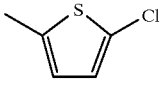 | 0.45 (I) | 245 | 83 |
| 31 | OCH$_3$ | H | 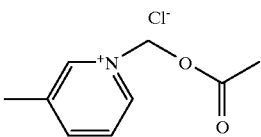 | 0.83 (X) | (amorph) | 16 |
| 32 | OCH$_3$ | H | 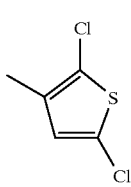 | 0.48 (I) | 247 | 75 |

TABLE 3-continued

Structure: X and Y substituents on benzofuran; 3-position has NH—CO—NH₂; 2-position has CO—R⁴

| Ex.-No. | Y | X | R4 | R_f | Mp °C. | Yield (% of theory) |
|---|---|---|---|---|---|---|
| 33 | OCH₃ | H | 3,4-dibromo-5-methylthiophen-2-yl | 0.46 (I) | 224 | 77 |
| 34 | OCH₃ | H | 5-bromo-2-methylthiophen-... | 0.42 (I) | 253 | 43 |
| 35 | OCH₃ | H | 3-bromo-2-methylthiophen-... | 0.42 (I) | >330 | 87 |
| 36 | CN | H | 2-methylthiophen-... | 0.38 (I) | 253 | 65 |
| 37 | NO₂ | H | 5-chloro-2-methylthiophen-... | 0.8 (V) | Z. 265 | 35 |
| 38 | NO₂ | H | 2-methylthiophen-... | 0.1 (II) | 235 | 45 |
| 39 | OCH₃ | H | 3,6-dichloro-2-methylpyridin-... | 0.15 (VIII) | 192 | 52 |
| 40 | OCH₃ | H | 2,5-dimethyl-4-methylthiophen-... | 0.63 (I), 0.84 (XII), 0.85 (XIII) | 210 | 53 |
| 41 | OCH₃ | H | 3-cyano-2-methylthiophen-... | 0.84 (XIII), 0.81 (XIII) | 243 | 98 |

TABLE 3-continued

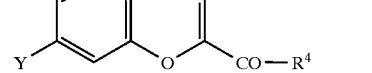

| Ex.-No. | Y | X | R4 | $R_f$ | Mp °C. | Yield (% of theory) |
|---|---|---|---|---|---|---|
| 42 | $NO_2$ | H |  | 0.82 (I)<br>0.85 (XII)<br>0.81 (XIII) | 200 | 40 |
| 43 | CN | H | 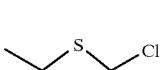 | 0.86 (XII)<br>0.85 (XIII) | 268 | 79 |
| 44 |  | H | 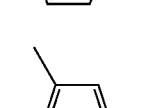 | 0.79 (I)<br>0.92 (XII)<br>0.92 (XIII) | 232 | 76 |

We claim:

1. A heterocyclylcarbonyl substituted benzofuranyl-urea of the formula (I):

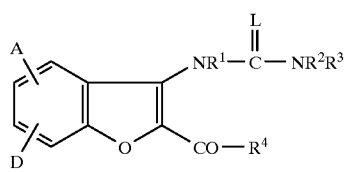

wherein

A and D are identical or different and represent hydrogen, straight-chain or branched alkoxycarbonyl having up to 4 carbon atoms, straight-chain or branched alkyl having up to 3 carbon atoms, which is unsubstituted or is substituted by carboxyl or alkoxycarbonyl each having up to 4 carbon atoms, phenoxy or benzoyl, or represent fluorine, chlorine, bromine, carboxyl, cyano, nitro, trifluoromethyl, trifluoromethoxy or a group of a formula —$OR_5$, in which $R^5$ denotes hydrogen or straight-chain or branched alkyl or alkenyl each having up to 6 carbon atoms, $R^1$ represents hydrogen or straight-chain or branched alkyl having up to 3 carbon atoms or a group of the formula —CO—$R^{14}$, in which $R^{14}$ denotes hydroxyl or straight chain or branched alkoxycarbonyl having up to 3 carbon atoms, L represents an oxygen or sulfur atom, $R^2$ and $R^3$ are identical or different and represent hydrogen, straight-chain or branched alkyl, alkoxycarbonyl or alkenyl each having up to 5 carbon atoms, or represent benzoyl or phenyl, which are unsubstituted or are substituted by identical or different substituents from the group consisting of fluorine, chlorine, bromine, carboxy, cyano, nitro or by a straight-chain or branched alkyl, alkoxy or alkoxycarbonyl each having up to 3 carbon atoms, and $R^4$ represents pyridyl, which is unsubstituted or is up to trifold substituted by identical or different substituents from the group consisting of pyridyl, fluorine, chlorine, bromine, methoxy, nitro, trifluoromethyl, cyano, or by straight-chain or branched alkyl having up to 3 carbon atoms, which is unsubstituted or is substituted by carboxyl or straight-chain or branched alkoxycarbonyl having up to 3 carbon atoms, or a salt thereof.

2. A compound according to claim 1 wherein such compound is N-[3-(6-methoxy-2-(3,5-dichloropyridine-2-carbonyl)-benzofuranyl)]urea of the formula

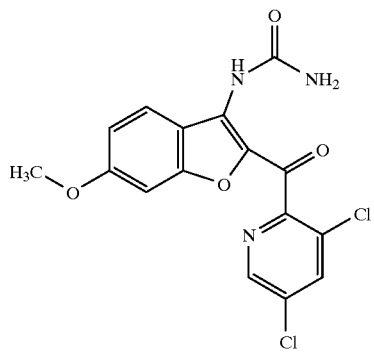

or a salt thereof.

3. A compound according to claim 1 wherein such compound is N-[3-(6-methoxy-2-(2,6-dimethylpyridine-3-carbonyl)benzofuranyl)]urea of the formula or a salt thereof.

4. A compound according to claim 1 wherein such compound is N-[3-(6-methoxy-2-(pyridine-3-carbonyl)-benzofuranyl)]urea of the formula

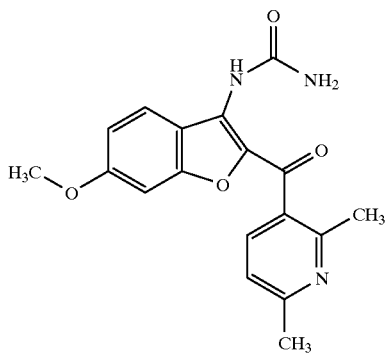

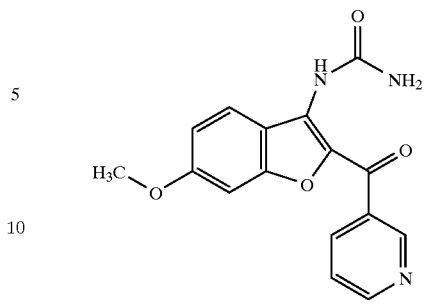

or a salt thereof.

5. A composition for the inhibition of phosphodiesterase IV comprising an amount effective therefore of a compound or a salt thereof according to claim 1 and a pharmacologically acceptable diluent.

6. The method of inhibition of phosphodiesterase IV in a patient in need thereof which comprises administering to such patient an amount effective therefor of a compound or a salt thereof according to claim 1.

* * * * *

UNITED STATES PATENT AND TRADEMARK OFFICE
CERTIFICATE OF CORRECTION

PATENT NO : 5,922,740
DATED : July 13, 1999
INVENTOR(S): Gabriele Braunlich et al.

It is certified that error appears in the above-identified patent and that said Letters Patent is hereby corrected as shown below:

Column 31, line 51, cancel "$OR_5$" and substitute --$OR^5$--

Signed and Sealed this

Fourth Day of January, 2000

Attest:

Attesting Officer

*Acting Commissioner of Patents and Trademarks*